(12) United States Patent
Trubetskoy et al.

(10) Patent No.: US 7,033,607 B2
(45) Date of Patent: *Apr. 25, 2006

(54) PH-TITRATABLE POLYAMPHOLYTES FOR DELIVERING POLYIONS TO A CELL

(75) Inventors: Vladimir S. Trubetskoy, Madison, WI (US); James E. Hagstrom, Middleton, WI (US); Vladimir G. Budker, Middleton, WI (US); Jon A. Wolff, Madison, WI (US); David B. Rozema, Madison, WI (US); Sean D. Monahan, Madison, WI (US)

(73) Assignee: Mirus Bio Corporation, Madison, WI (US)

( * ) Notice: Subject to any disclaimer, the term of this patent is extended or adjusted under 35 U.S.C. 154(b) by 402 days.

This patent is subject to a terminal disclaimer.

(21) Appl. No.: 10/095,789

(22) Filed: Mar. 11, 2002

(65) Prior Publication Data

US 2003/0008009 A1    Jan. 9, 2003

Related U.S. Application Data

(63) Continuation-in-part of application No. 09/753,990, filed on Jan. 2, 2001, now Pat. No. 6,383,811.

(60) Provisional application No. 60/174,132, filed on Dec. 31, 1999.

(51) Int. Cl.
*A61K 9/127* (2006.01)
*A61K 31/713* (2006.01)

(52) U.S. Cl. .................. 424/450; 514/44; 435/458; 435/456; 435/472

(58) Field of Classification Search ............. 424/450; 435/458, 456, 472
See application file for complete search history.

(56) References Cited

U.S. PATENT DOCUMENTS 6,383,811 B1 *   5/2002   Wolff et al. .............. 424/450

* cited by examiner

*Primary Examiner*—James Ketter
(74) *Attorney, Agent, or Firm*—Mark K. Johnson; Kirk Ekena

(57) ABSTRACT

A polyampholyte is utilized in a condensed polynucleotide complex for purposes of nucleic acid delivery to a cell. The complex can be formed with an appropriate amount of positive and/or negative charge such that the resulting complex can be delivered to the extravascular space and may be further delivered to a cell.

20 Claims, No Drawings

PH-TITRATABLE POLYAMPHOLYTES FOR DELIVERING POLYIONS TO A CELL

This Application is a Continuation-In-Part of Ser. No. 09/753,990 filed on Jan. 2, 2001, now U.S. Pat. No. 6,383,811, which claims benefit of U.S. Provisional Application No. 60/174,132, filed Dec. 31, 1999.

FIELD OF THE INVENTION

The invention relates to compounds and methods for use in biologic systems. More particularly, polyions that are protonatable under physiological conditions are utilized for modifying the charge of particles, such as molecules, polymers, nucleic acids and genes for delivery to cells.

BACKGROUND

Polymers are used for drug delivery for a variety of therapeutic purposes. Polymers have also been used in research for delivery of nucleic acids (polynucleotides and oligonucleotides) to cells, the process is one step in reaching a goal of providing therapeutic processes (gene therapy). One of the several methods of nucleic acid delivery to the cells is the use of DNA-polyion complexes. It has been shown that cationic proteins like histones and protamines or synthetic polymers like polylysine, polyarginine, polyornithine, DEAE dextran, polybrene, and polyethylenimine may be effective intracellular delivery agents while small polycations like spermine are ineffective.

In terms of intravenous injection, DNA must cross the endothelial barrier and reach the parenchymal cells of interest. The largest endothelia fenestrae (holes in the endothelial barrier) occur in the liver and have an average diameter from 75–150 nm. The trans-epithelial pores in other organs are much smaller, for example, muscle endothelium can be described as a structure which has a large number of small pores with a radius of 4 nm, and a very low number of large pores with a radius of 20–30 nm. The size of the DNA complexes is also important for the cellular uptake process. After binding to the target cells the DNA-polycation complex should be taken up by endocytosis.

Applicants have provided a process for delivering a compound across the endothelial barrier to the extravascular space and then to a cell.

SUMMARY

Described in a preferred embodiment is a process for enhancing delivery of a polyion to a cell, comprising the formation of a complex of polyampholyte and polyion. Then, delivering the complex into a cell.

In another preferred embodiment, we describe a process for extravasation of a complex. The process comprises the formation of a complex of polyampholyte and polyion. Then, inserting the complex into a vessel and delivering the complex to an extravascular space.

Reference is now made in detail to the preferred embodiments of the invention, examples of which are illustrated in the accompanying drawings.

DETAILED DESCRIPTION

Polyampholytes are copolyelectrolytes containing both polycations and polyanions in the same polymer. In aqueous solutions polyampholytes are known to precipitate near the isoelectric point and form micelle-like structures (globules) at the excess of either charge. Such globules maintain tendency to bind other charged macromolecules and particles (see R R Netz, J F Joanny, Macromolecules, 31, 5123–5141 (1998)).

In provisional application Ser. No. 60/093,153 we described gene transfer activity which can be substantially increased by adding polyanions to preformed DNA/polycation complexes(i.e. recharging). We confirmed the same phenomenon for cationic lipids (provisional application Ser. No. 60/150,160). We extended this principle into situations where DNA-binding polycation and polyanion are covalently linked into one polymer. In this application we investigated the use of polyampholytes that contain pH-titratable functional groups.

It has previously been demonstrated that binding of negatively-charged serum components can significantly decrease gene transfer efficacy of DNA/polycation (DNA/pC) complexes in vivo (Vitiello L, Bockhold K, Joshi P B, Worton P B, Gene Therapy 5, 1306–13 (1998); Ross P C, Hui S W, Gene Therapy 6, 651–659 (1999). We have found that addition of polyanions to the point of near complex charge reversal drastically increases the efficacy of gene transfer mediated by DNA/pC complex upon i/v administration in mice (Provisional application Ser. No. 60/093,153). This improvement takes place due to protecting effect of pA that decreases the charge of the complex, thereby inhibiting interactions with negatively charged serum components. We believe that gene transfer increase observed with DNA/polyampholyte complexes may be based on the same phenomenon by decreasing the charge of the DNA-polycation complex.

Formation of Polyampholytes

Conceptually, there are several ways in which one may form polyampholytes: monovalent block polyampholytes, multivalent block polyampholytes, alternating copolyampholytes and random copolyampholytes. All of these ways of constructing polyampholytes are equivalent in that they result in the formation of a polyampholyte.

Monovalent block polyampholytes are polyampholytes in which one covalent bond connects a polycation to a polyanion. Cleavage of this bond results in the formation of a polycation and a polyanion. For each polyelectrolyte there may be more than one attached polyelectrolyte of opposite charge, but the attachement between polymers is through one covalent bond.

Multivalent block polyampholytes are polyampholytes in which more than one bond connects polycation to polyanion. Cleavage of these bonds results in a polycation and a polyanion. A name for the process of connecting preformed polycations and polyanions into a multivalent block polyampholyte is crosslinking. For each polyelectrolyte there may be more than one attached polyelectrolyte of opposite charge, but the attachment between polymers is through one covalent bond.

Alternating copolyampholytes are polyampholytes in which the cationic and anionic monomers repeat in an alternating sequence. The monomers in these polyampholytes may, but need not be, polymers themselves. Cleavage of the bonds between monomers results in anions and cations or polyanions and polycations (if the monomers are polycations and polyanions).

Random copolyampholytes are polyampholytes in which the cationic and anionic monomers repeat in a random fashion. The monomers in these polyampholytes may, but need not be, polymers themselves. Cleavage of the bonds between monomers results in anions and cations or polyanions and polycations (if the monomers are polycations and polycations).

Charges of polyamphophiles

Polyampholytes may have an excess of on charge or another. For example, a polyamphiphile may contain more anionic groups than cationic groups and be, therefore, net anionic. Such a polyampholyte is termed an anionic polyampholytes. In the same way, a cationic polyampholyte contains more cationic groups than anionic groups. If a polyampholyte is composed of groups whose charge is dependent upon protonation/deprotonation for charge, then the charge of the polyampholyte itself is dependent on protonation/deprotonation, which is dependent on the pH of the solution.

The present invention is related to the formation of DNA/polyampholyte complexes in which the polyampholyte contains function groups that are titratable, i.e. accept/donate protons, under physiological conditions.

PREFERRED EMBODIMENTS

The following description provides exemplary embodiments of the systems, compositions, and methods of the present invention. These embodiments include a variety of systems that have been demonstrated as effective delivery systems both in vitro and in vivo. The invention is not limited to these particular embodiments.

Polyampholytes Containing Groups Titratable at Physiological pH.

DNA delivery systems are often designed to be sensitive to the acidic environment of the endosome in order to bring about endosomal release of the DNA. Specifically, incorporation of functional groups which are protonated in the pH range 5–7 (the pH range in the endosome) causes the charge of the DNA delivery system to change as the pH changes. This "buffering" of the endosome by the DNA delivery system causes an increase in the amount of protons needed for a drop in pH. It is postulated that this increase in the amount of protons causes a swelling and bursting of the endosome. This buffering and swelling of the endosome is one hypothesized to be the means by which polyethylenimine aids in DNA transfection. Polyethylenimine's high density of amine functional groups results in large number of the amine groups being unprotonated at physiological pH. These amine groups have pKa values that are not in the normal range for amines, 9–11, but are in the range 5–7. As a consequence polyethylenimine buffers in the pH range of the endosome.

Polyethylenimine's ability to buffer in the pH range 5–7 is the result of close proximity of function groups in a polymer. Another approach to create polymers containing pH-titratable groups is to incorporate into the gene delivery vehicle function groups that buffer in the pH range 4–8. A functional group that buffers in that range is an imidazole group. Imidazole groups have a pKa that is roughly 7.

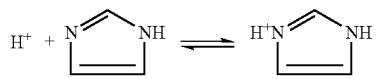

Imidazoles groups may be incorporated into polyampholytes by coupling them to polyanions. Such a polyampholyte will be negatively-charged at high pH and positively charged at low pH. The point of neutrality depends upon the ratio of anionic groups to imidazole. For example, one would expect that a polyampholyte containing one to one ratio of imidazoles to carboxylic acid groups would be neutral at roughly pH 6, anionic at higher pH, and cationic at lower pH. This polyampholyte's charge would transition exactly in the same pH range of the endosome. The transition in charge is potentially endosome disruptive due to the buffering ability of the pH-titratable groups and also the increased interaction between a positively-charged particle and the negatively-charge endosome membrane. We have synthesized such polymers and they, indeed, increase the gene transfer activity of DNA particles.

A method for synthesizing such a polyampholyte is to react amine-containing compounds with poly (methylvinylether maleic anhydride) pMVMA. The anhydride of pMVMA reacts with amines to form an amide and an acid. Two different amine and imidazole containing compounds were used: histidine, which also attaches a carboxylic acid group, and histamine which just attaches an imidazole group. The histidine containing polymer was given the Mirus Corporation number 486 (MC#486) and the histamine containing polymer was given the Mirus Corporation number 510 (MC#510). These polyampholytes are alternating copolyampholytes.

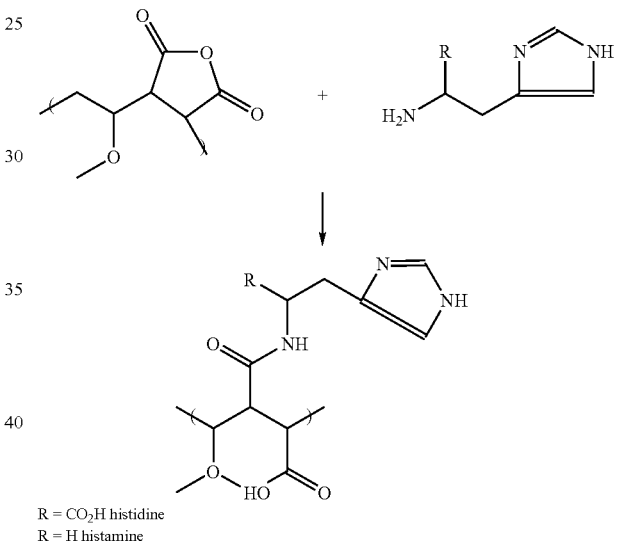

R = CO$_2$H histidine
R = H histamine

To determine the effect of pH on these polyampholytes, we measured the amount of polymer needed to condense fluorescein-labeled polylysine at pH 7.5 and pH 6.0. As fluorescein-labeled polylysine is condensed by addition of a negatively charged polyelectrolyte the fluorescein fluorophores are brought closer together, which causes fluorescence to be quenched. This quenching enables one to measure the extent of condensation the charge density of the polyelectrolyte. The histamine containing polymer, MC#510, required significantly more material to condense the polylysine at pH 6.0 than at pH 7.5. Approximately five-fold more polymer is required. The histidine-containing polymer, MC#486, also need more material at pH 6.0, approximately two-fold more. These data suggest that we have made polyanions which are pH-sensitive in a pH range that is important for endosomal release. Addition of these polyampholytes to polycation-condensed DNA result in large increases in gene delivery both in cell culture and in vivo.

Another preferred embodiment is the formation of a block polyampholyte with between polycations and polyanions that contain pH-titratable groups. Either constituent polymer or both polymers may contain pH-titratable groups, but covalent attachment of the polymers results in a pH-titratable polyampholyte. Examples of polycations that contain the pH-titratable imidazole group include polyhistidine, copolymers of histidine and polylysine, and imidazole-modified and histidylated polyamines (polyarnines that have had their side chains modified to attach imidazole groups or histidine groups). An example of these modified polyamines is the acylation of polyamines poly-L-lysine (PLL) and polyallylamine with imidazole acetic acid. Polymers MC#510 and MC#486 are examples of imidazole-containing polymer with net negative charge. Examples of a polyanions that contain pH-titratable groups include any polymer containing carboxylic acid groups (pKa ca 4–5) such as polyaspartic acid, polyglutamic acid, succinylated PLL, polyacrylic acid, and polymethacrylic acid.

Formation of a covalent bond (or bonds) between polycations and polyanions containing pH-titratable groups results in the formation of a polyampholyte containing pH-titratable group. If one bond is formed is it a monovalent block polyampholyte and if more than one bond is formed then there is the formation of a multivalent block polyampholyte. Another preferred embodiment is the formation of a multivalent block polyampholyte from the polyeation and the net-negatively charged polyampholyte polymer MC#510. Formation of amide bonds between the amine groups of PLL and the carboxylate groups of polymer MC#510 by addition of a carbodiimide results in the formation of a multivalent block polyampholyte. This multivalent block polyampholyte has superior transfection ability to PLL-condensed DNA particles both in vivo and in tissue culture. In addition, this polyampholyte is, depending on the conditions, is superior to complexation of polymer MC#510 to PLL-condensed DNA.

In one preferred embodiment, polycations are selected from the group including but not limited to poly-L-lysine, poly-D-lysine, poly-L,D-lysine, polyethylenimine (linear and/or branched), polyallylamine, poly-L-ornithine, poly-D-ornithine, poly-L,D-ornithine, polyvinylamine, natural cationic proteins, synthetic cationic proteins, synthetic cationic peptides and synthetic polymers containing monomers with amines selected from but not limited to alkylamine, aryl amine, aralkylamine, imidazole, pyridine, and piperazine, pyrazine, pyrimidine, oxazoline, oxazole, oxazolidine.

In another perferred embodiement, polyanions are selected from the group including but not limited to poly-L-aspartic acid, poly-D-aspartic acid, poly-L,D-aspartic acid, polyacrylic acid, poly-L-glutamic acid, poly-D-glutamic acid, poly-L,D-glutamic acid, succinylated poly-L-lysine, succinylated poly-D-lysine, succinylated poly-L,D-lysine, succinylated polyethyleneimine, succinylated polyallylamine, succinylated poly-L-ornithine, succinylated poly-D-ornithine, succinylated poly-L,D-ornithine, succinylated polyvinylamine, polymethacrylic acid, dextran sulfate, heparin, hyaluronic acid, DNA, RNA, natural anionic proteins, synthetic anionic proteins, synthetic anionic peptides, and synthetic polymers continuing monomers in which an amine has been reacted with a substructure of succinic anhydride.

Definitions

To facilitate an understanding of the present invention, a number of terms and phrases are defined below:

Groups Titratable at Physiological pH

Groups titratable at physiological pH (also called pH-titratable groups) are chemical functional groups that lose/gain a proton in water in the pH range 4–8. Groups titratable at physiological pH act as buffers within the pH range of 4–8. Groups titratable at physiological pH can be determined experimentally by conducting an acid-base titration and experimentally determining if the group buffers within the pH-range of 4–8. Examples of chemical functional groups that can exhibit buffering within this pH range include but are not limited to carboxylic acids, imidazole, N-substituted imidazole, pyridine, phenols, and polyamines. Groups titratable at physiological pH can include polymers, non-polymers, peptides, modified peptides, proteins, and modified proteins.

Biologically Active Compound

A biologically active compound is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. In this specification, the cellular production of, or inhibition of a material, such as a protein, caused by a human assisting a molecule to an in vivo cell is an example of a delivered biologically active compound. Pharmaceuticals, proteins, peptides, polypeptides, enzyme inhibitors, hormones, cytokines, antigens, viruses, oligonucleotides, enzymes and nucleic acids are examples of biologically active compounds.

Peptide and polypeptide refer to a series of amino acid residues, more than two, connected to one another by amide bonds between the beta or alpha-amino group and carboxyl group of contiguous amino acid residues. The amino acids may be naturally occurring or synthetic. Polypeptide includes proteins and peptides, modified proteins and peptides, and non-natural proteins and peptides. Enzymes are proteins evolved by the cells of living organisms for the specific function of catalyzing chemical reactions. A chemical reaction is defined as the formation or cleavage of covalent or ionic bonds. Bioactive compounds may be used interchangeably with biologically active compound for purposes of this application.

Delivery of Biologically Active Compound

The delivery of a biologically active compound is commonly known as "drug delivery". "Delivered" means that the biologically active compound becomes associated with the cell or organism. The compound can be in the circulatory system, intravessel, extracellular, on the membrane of the cell or inside the cytoplasm, nucleus, or other organelle of the cell.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter. An intravascular route of administration enables a polymer or polynucleotide to be delivered to cells more evenly distributed and more efficiently expressed than direct injections. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, and bile ducts. The intravascular route includes delivery through the blood vessels such as an artery or a vein. An administration route involving the mucosal membranes is meant to include nasal, bronchial, inhalation into the lungs, or via the eyes. Other routes of administration include intraparenchymal into tissues such as muscle (intramuscular), liver, brain, and kidney. Transdermal routes of administration have been effected by patches and ionotophoresis. Other epithelial routes include oral, nasal, respiratory, and vaginal routes of administration.

Delivery System

Delivery system is the means by which a biologically active compound becomes delivered. That is all compounds, including the biologically active compound itself, that are required for delivery and all procedures required for delivery including the form (such volume and phase (solid, liquid, or gas)) and method of administration (such as but not limited to oral or subcutaneous methods of delivery).

Nucleic Acid

The term "nucleic acid" is a term of art that refers to a polymer containing at least two nucleotides. "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides. Nucleotides are the monomeric units of nucleic acid polymers. A "polynucleotide" is distinguished here from an "oligonucleotide" by containing more than 80 monomeric units, oligonucleotides contain from 2 to 80 nucleotides. The term nuclei acid includes deoxyribonucleic acid (DNA) and ribonucleic acid (RNA). The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxy-aminomethyl-2-thiourscil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

DNA may be in the form of anti-sense, plasmid DNA, parts of a plasmid DNA, product of a polymerase chain reaction (PCR), vectors (P1, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), anti-sense RNA, ribozymes, chimeric sequences, or derivatives of these groups.

"Anti-sense" is a polynucleotide that interferes with the function of DNA and/or RNA. This may result in suppression of expression. Natural nucleic acids have a phosphate backbone, artificial nucleic acids may contain other types of backbones and bases. These include PNAs (peptide nucleic acids), phosphothionates, morpholino and other variants of the phosphate backbone of native nucleic acids. In addition, DNA and RNA may be single, double, triple, or quadruple stranded.

The term "recombinant DNA molecule" as used herein refers to a DNA molecule that is comprised of segments of DNA joined together by means of molecular biological techniques. "Expression cassette" refers to a natural or recombinantly produced polynucleotide molecule that is capable of expressing protein(s). A DNA expression cassette typically includes a promoter (allowing transcription initiation), and a sequence encoding one or more proteins. Optionally, the expression cassette may include transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences.

A nucleic acid can be used to modify the genomic or extrachiromosomal DNA sequences. This can be achieved by delivering a nucleic acid that is expressed. Alternatively, the nucleic acid can effect a change in the DNA or RNA sequence of the target cell. This can be achieved by homologous recombination, gene conversion, or other yet to be described mechanisms.

Gene

The term "gene" refers to a nucleic acid (e.g., DNA) sequence that comprises coding sequences necessary for the production of a polypeptide or precursor (e.g., -myosin heavy chain). The polypeptide can be encoded by a fall length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form.

Gene Expression

As used herein, the term "gene expression" refers to the process of converting genetic information encoded in a gene into RNA (e.g., mRNA, rRNA, tRNA, or snRNA) through "transcription" of the gene (i. e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decreases production. Molecules (e.g., transcription factors) that are involved in up-regulation or down-regulation are often called "activators" and "repressors," respectively.

Delivery of Nucleic Acids

The process of delivering a polynucleotide to a cell has been commonly termed "transfection" or the process of "transfecting" and also it has been termed "transformation". The polynucleotide could be used to produce a change in a cell that can be therapeutic. The delivery of polynucleotides or genetic material for therapeutic and research purposes is commonly called "gene therapy". The delivery of nucleic acid can lead to modification of the DNA sequence of the target cell.

The polynucleotides or genetic material being delivered are generally mixed with transfection reagents prior to delivery. The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has irreversibly integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA. The term "naked polynucleotides" indicates that the polynucleotides are not associated with a transfection reagent or other delivery vehicle that is required for the polynucleotide to be delivered to a cell.

A "transfection reagent" or "delivery vehicle" is a compound or compounds that bind(s) to or complex(es) with oligonucleotides, polynucleotides, or other desired compounds and mediates their entry into cells. Examples of transfection reagents include, but are not limited to, cationic liposomes and lipids, polyamines, calcium phosphate precipitates, histone proteins, polyethylenimine, and polylysine complexes (polyethylenimine and polylysine are both toxic). Typically, when used for the delivery of nucleic acids, the transfection reagent has a net positive charge that binds to the polynucleotide's negative charge. For example, cationic liposomes or polylysine complexes have net positive charges that enable them to bind to DNA or RNA.

Hydrophobic Stabilization

Hydrophobic stabilization means the stability gained in a complex in water due to the noncovalent interactions between hydrophobic groups in the system.

Lipid

Any of a diverse group of organic compounds that are insoluble in water, but soluble in organic solvents such as chloroform and benzene. Lipids contain both hydrophobic and hydrophilic sections. Lipids is meant to include complex lipids, simple lipids, and synthetic lipids.

Complex Lipids

Complex lipids are the esters of fatty acids and include glycerides (fats and oils), glycolipids, phospholipids, and waxes.

Simple Lipids

Simple lipids include steroids and terpenes.

Synthetic Lipids

Synthetic lipids includes amides prepared from fatty acids wherein the carboxylic acid has been converted to the amide, synthetic variants of complex lipids in which one or more oxygen atoms has been substituted by another heteroatom (such as Nitrogen or Sulfur), and derivatives of simple lipids in which additional hydrophilic groups have been chemically attached. Synthetic lipids may contain one or more labile groups.

Fats

Fats are glycerol esters of long-chain carboxylic acids. Hydrolysis of fats yields glycerol and a carboxylic acid—a fatty acid. Fatty acids may be saturated or unsaturated (contain one or more double bonds).

Oils

Oils are esters of carboxylic acids or are glycerides of fatty acids.

Glycolipids

Glycolipids are sugar containing lipids. The sugars are typically galactose, glucose or inositol.

Phospholipids

Phospholipids are lipids having both a phosphate group and one or more fatty acids (as esters of the fatty acid). The phosphate group may be bound to one or more additional organic groups.

Wax

Waxes are any of various solid or semisolid substances generally being esters of fatty acids.

Fatty Acids

Fatty acids are considered the hydrolysis product of lipids (fats, waxes, and phosphoglycerides).

Hydrophobic Groups

Hydrophobic groups indicate in qualitative terms that the chemical moiety is water-avoiding. Typically, such chemical groups are not water soluble, and tend not to form hydrogen bonds.

Hydrophilic Groups

Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides, and groups containing amines, amides, alkoxy amides, carboxylic acids, sulfurs, or hydroxyls.

Enzyme

Enzyme is a protein that acts as a catalyst. That is a protein that increases the rate of a chemical reaction without itself undergoing any permanent chemical change. The chemical reactions that are catalyzed by an enzyme are termed enzymatic reactions and chemical reactions that are not are termed nonenzymatic reactions.

Complex

Two molecules are combined, to form a complex through a process called complexation or complex formation, if the are in contact with one another through noncovalent interactions such as electrostatic interactions, hydrogen bonding interactions, and hydrophobic interactions.

Modification

A molecule is modified, to form a modification through a process called modification, by a second molecule if the two become bonded through a covalent bond. That is, the two molecules form a covalent bond between an atom form one molecule and an atom from the second molecule resulting in the formation of a new single molecule. A chemical covalent bond is an interaction, bond, between two atoms in which there is a sharing of electron density.

Cell Targeting Signals

Cell targeting signal (or abbreviated as the Signal) is defined in this specification as a molecule that modifies a biologically active compounds such as drug or nucleic acid and can direct it to a cell location (such as tissue) or location in a cell (such as the nucleus) either in culture or in a whole organism. By modifying the cellular or tissue location of the foreign gene, the function of the biologically active compound can be enhanced.

The cell targeting signal can be a protein, peptide, lipid, steroid, sugar, carbohydrate, (non-expressing) polynucleic acid or synthetic compound. The cell targeting signal enhances cellular binding to receptors, cytoplasmic transport to the nucleus and nuclear entry or release from endosomes or other intracellular vesicles.

Nuclear localizing signals enhance the targeting of the pharmaceutical into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus. For example, karyopherin beta itself could target the DNA to the nuclear pore complex. Several peptides have been derived from the SV40 T antigen. These include a short NLS (H-CGYGPKKKRKVGG-OH, SEQ ID 1) or long NLS's (H-CKKKSSSDDEATAD-SQHSTPPKKKRKVEDPKDFPSELLS-OH, SEQ ID 2 and H-CKKKWDDEATADSQHSTPPKKKRKVEDP-KDFPSELLS-OH, SEQ ID 3). Other NLS peptides have been derived from M9 protein (CYNDFGNYNNQSSNF-GPMKQGNFGGRSSGPY, SEQ ID 4), E1A (H-CKRGP-KRPRP-OH, SEQ ID 5), nucleoplasmin (H-CK-KAVKRPAATKKAGQAKKKKL-OH, SEQ ID 6), and c-myc (H-CKKKGPAAKRVKLD-OH, SEQ ID 7).

Signals that enhance release from intracellular compartments (releasing signals) can cause DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin A1 and the ER-retaining signal (KDEL sequence, SEQ ID 8), viral components such as influenza virus hemagglutinin subunit HA-2 peptides and other types of amphipathic peptides.

Cellular receptor signals are any signal that enhances the association of the biologically active compound with a cell. This can be accomplished by either increasing the binding of the compound to the cell surface and/or its association with an intracellular compartment, for example: ligands that enhance endocytosis by enhancing binding the cell surface. This includes agents that target to the asialoglycoprotein receptor by using asiologlycoproteins or galactose residues. Other proteins such as insulin, EGF, or transferrin can be used for targeting. Peptides that include the RGD sequence can be used to target many cells. Chemical groups that react with thiol, sulfhydryl, or disulfide groups on cells can also be used to target many types of cells. Folate and other vitamins can also be used for targeting. Other targeting groups include molecules that interact with membranes such as lipids, fatty acids, cholesterol, dansyl compounds, and amphotericin derivatives. In addition viral proteins could be used to bind cells.

Interaction Modifiers

An interaction modifier changes the way that a molecule interacts with itself or other molecules, relative to molecule containing no interaction modifier. The result of this modification is that self-interactions or interactions with other molecules are either increased or decreased. For example cell targeting signals are interaction modifiers with change the interaction between a molecule and a cell or cellular component. Polyethylene glycol is an interaction modifier that decreases interactions between molecules and themselves and with other molecules.

Reporter or Marker Molecules

Reporter or marker molecules are compounds that can be easily detected. Typically they are fluorescent compounds such as fluorescein, rhodamine, Texas red, cy 5, cy 3 or dansyl compounds. They can be molecules that can be detected by infrared, ultraviolet or visible spectroscopy or by antibody interactions or by electron spin resonance. Biotin is another reporter molecule that can be detected by labeled avidin. Biotin could also be used to attach targeting groups.

Linkages

An attachment that provides a covalent bond or spacer between two other groups (chemical moieties). The linkage may be electronically neutral, or may bear a positive or negative charge. The chemical moieties can be hydrophilic or hydrophobic. Preferred spacer groups include, but are not limited to C1–C12 alkyl, C1–C12 alkenyl, C1–C12 alkynyl, C6–C18 aralkyl, C6–C18 aralkenyl, C6–C18 aralkynyl, ester, ether, ketone, alcohol, polyol, amide, amine, polyglycol, polyether, polyamine, thiol, thio ether, thioester, phosphorous containing, and heterocyclic. The linkage may or may not contain one or more labile bonds.

Labile Bond

A labile bond is a covalent bond that is capable of being selectively broken. That is, the labile bond may be broken in the presence of other covalent bonds without the breakage of other covalent bonds. For example, a disulfide bond is capable of being broken in the presence of thiols without cleavage of any other bonds, such as carbon-carbon, carbon-oxygen, carbon-sulfur, carbon-nitrogen bonds, which may also be present in the molecule. Labile also means cleavable.

Labile Linkage

A labile linkage is a chemical compound that contains a labile bond and provides a link or spacer between two other groups. The groups that are linked may be chosen from compounds such as biologically active compounds, membrane active compounds, compounds that inhibit membrane activity, functional reactive groups, monomers, and cell targeting signals. The spacer group may contain chemical moieties chosen from a group that includes alkanes, alkenes, esters, ethers, glycerol, amide, saccharides, polysaccharides, and heteroatoms such as oxygen, sulfur, or nitrogen. The spacer may be electronically neutral, may bear a positive or negative charge, or may bear both positive and negative charges with an overall charge of neutral, positive or negative.

pH-Labile Linkages and Bonds pH-labile refers to the selective breakage of a covalent bond under acidic conditions (pH<7). That is, the pH-labile bond may be broken under acidic conditions in the presence of other covalent bonds without their breakage. The term pH-labile includes both linkages and bonds that are pH-labile, very pH-labile, and extremely pH-labile.

Amphiphilic and Amphipathic Compounds

Amphipathic, or amphiphilic, compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bonds. Hydrocarbons are hydrophobic groups.

Membrane Active or Membrane Disruptive Compound

Membrane active or membrane disruptive agents or compounds are compounds (typically a polymer, peptide or protein) that are able alter the membrane structure. This change in structure can be shown by the compound inducing one or more of the following effects upon a membrane: an alteration that allows small molecule permeability, pore formation in the membrane, a fusion and/or fission of membranes, an alteration that allows large molecule permeability, or a dissolving of the membrane. This alteration can be functionally defined by the compound's activity in at least one the following assays: red blood cell lysis (hemolysis), liposome leakage, liposome fusion, cell fusion, cell lysis and endosomal release. An example of a membrane disruptive agent in our examples is the peptide melittin, whose membrane activity is demonstrated by its ability to release heme from red blood cells (hemolysis). In addition, dimethylmaleamic-modified melittin(DM-Mel) reverts to melittin in the acidic environment of the endosome causes endosomal release as seen by the diffuse staining of fluorescein-labeled dextran in our endosomal release assay.

More specifically membrane active compounds allow for the transport of molecules with molecular weight greater than 50 atomic mass units to cross a membrane. This transport may be accomplished by either the total loss of membrane structure, the formation of holes (or pores) in the membrane structure, or the assisted transport of compound through the membrane. In addition, transport between liposomes, or cell membranes, may be accomplished by the fusion of the two membranes and thereby the mixing of the contents of the two membranes.

Derivative

Derivative, or substructure, means the chemical structure of the compound and any compounds derived from that chemical structure from the replacement of one or more hydrogen atoms by any other atom or change in oxidation state. For example if the substructure is succinic anhydride, then methylsuccinic anhydride, 2,2-dimethylsuccinic anhydride, 3-oxabicyclo[3.1.0]hexane-2,4-dione, maleic anhydride, citriconic anhydride, and 2,3-dimethylmaleic anhydride have the same substructure, or are derivatives.

Polymers

A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

The main chain of a polymer is composed of the atoms whose bonds are required for propagation of polymer length. For example in PLL, the carbonyl carbon, α-carbon, and α-amine groups are required for the length of the polymer and are therefore main chain atoms. The side chain of a polymer is composed of the atoms whose bonds are not required for propagation of polymer length. For example in PLL, the β, γ, δ, and ε-carbons, and ε-nitrogen are not required for the propagation of the polymer and are therefore side chain atoms.

To those skilled in the art of polymerization, there are several categories of polymerization processes that can be utilized in the described process. The polymerization can be chain or step. This classification description is more often used that the previous terminology of addition and condensation polymer. "Most step-reaction polymerizations are condensation processes and most chain-reaction polymerizations are addition processes" (M. P. Stevens Polymer Chemistry: An Introduction New York Oxford University Press 1990). Template polymerization can be used to form polymers from daughter polymers.

Step Polymerization:

In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed.

Typically, step polymerization is done either of two different ways. One way, the monomer has both reactive functional groups (A and B) in the same molecule so that A-B yields -[A-B]-

Or the other approach is to have two difunctional monomers.

A-A+B-B yields -[A-A-B-B]-

Generally, these reactions can involve acylation or alkylation. Acylation is defined as the introduction of an acyl group (—COR) onto a molecule. Alkylation is defined as the introduction of an alkyl group onto a molecule.

If functional group A is an amine then B can be (but not restricted to) an isothiocyanate, isocyanate, acyl azide, N-hydroxysuccinimide, sulfonyl chloride, aldehyde (including formaldehyde and glutaraldehyde), ketone, epoxide, carbonate, imidoester, carboxylate, or alkylphosphate, arylhalides (difluoro-dinitrobenzene), anhydrides or acid halides, p-nitrophenyl esters, o-nitrophenyl pentachlorophenyl esters, or pentafluorophenyl esters. In other terms when function A is an amine then function B can be acylating or alkylating agent or amination.

If functional group A is a thiol, sulfhydryl, then function B can be (but not restricted to) an iodoacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group A is carboxylate then function B can be (but not restricted to) a diazoacetate or an amine in which a carbodiimide is used. Other additives may be utilized such as carbonyldiimidazole, dimethylaminopyridine, N-hydroxysuccinimide or alcohol using carbodiimide and dimethylaminopyridine.

If functional group A is a hydroxyl then function B can be (but not restricted to) an epoxide, oxirane, or an amine in which carbonyldiimidazole or N,N'-disuccinimidyl carbonate, or N-hydroxysuccinimidyl chloroformate or other chloroformates are used.

If functional group A is an aldehyde or ketone then function B can be (but not restricted to) an hydrazine, hydrazide derivative, amine (to form a imine or iminium that may or may not be reduced by reducing agents such as $NaCNBH_3$) or hydroxyl compound to form a ketal or acetal. Yet another approach is to have one difunctional monomer so that A-A plus another agent yields -[A-A]-.

If function A is a thiol, sulfhydryl, group then it can be converted to disulfide bonds by oxidizing agents such as iodine ($I_2$) or $NaIO_4$ (sodium periodate), or oxygen ($O_2$). Function A can also be an amine that is converted to a thiol, sulfhydryl, group by reaction with 2-Iminothiolate (Traut's reagent) which then undergoes oxidation and disulfide formation. Disulfide derivatives (such as a pyridyl disulfide or 5-thio-2-nitrobenzoic acid{TNB} derivatives) can also be used to catalyze disulfide bond formation.

Functional group A or B in any of the above examples could also be a photoreactive group such as aryl azides, halogenated aryl azides, diazo, benzophenones, alkynes or diazirine derivatives. Reactions of the amine, hydroxyl, thiol, sulfhydryl, carboxylate groups yield chemical bonds that are described as amide, amidine, disulfide, ethers, esters, enamine, urea, isothiourea, isourea, sulfonamide, carbamate, carbon-nitrogen double bond (imine), alkylamine bond (secondary amine), carbon-nitrogen single bonds in which the carbon contains a hydroxyl group, thio-ether, diol, hydrazone, diazo, or sulfone.

Chain Polymerization: In chain-reaction polymerization growth of the polymer occurs by successive addition of monomer units to limited number of growing chains. The initiation and propagation mechanisms are different and there is usually a chain-terminating step. The polymerization rate remains constant until the monomer is depleted.

Monomers containing vinyl, acrylate, methacrylate, acrylamide, methacrylamide groups can undergo chain reaction, which can be radical, anionic, or cationic. Chain polymerization can also be accomplished by cycle or ring opening polymerization. Several different types of free radical initiatiors could be used that include peroxides, hydroxy peroxides, and azo compounds such as 2,2'-Azobis(-amidino-propane) dihydrochloride (AAP). A compound is a material made up of two or more elements.

Types of Monomers: A wide variety of monomers can be used in the polymerization processes. These include positive charged organic monomers such as amines, imidine, guanidine, imine, hydroxylamine, hydrazine, heterocycles (like imidazole, pyridine, morpholine, pyrimidine, or pyrene. The amines could be pH-sensitive in that the $pK_a$ of the amine is within the physiologic range of 4 to 8. Specific amines include spermine, spermidine, N,N'-bis(2-aminoethyl)-1,3-propanediamine (AEPD), and 3,3'-Diamino-N,N-dimethyl-dipropylammonium bromide. Monomers can also be hydrophobic, hydrophilic or amphipathic. Monomers can also be intercalating agents such as acridine, thiazole organge, or ethidium bromide. Other Components of the Monomers and Polymers: The polymers have other groups that increase their utility. These groups can be incorporated into monomers prior to polymer formation or attached to the polymer after its formation. These groups include: Targeting Groups—such groups are used for targeting the polymer-nucleic acid complexes to specific cells or tissues. Examples of such targeting agents include agents that target to the asialoglycoprotein receptor by using asiologlycoproteins or galactose residues. Other proteins such as insulin, EGF, or transferrin can be used for targeting. Protein refers to a molecule made up of 2 or more amino acid residues connected one to another as in a polypeptide. The amino acids may be naturally occurring or synthetic. Peptides that include the RGD sequence can be used to target many cells. Chemical groups that react with thiol, sulfhydryl, or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives. After interaction of the supramolecular complexes with the cell, other targeting groups can be used to increase the delivery of the drug or nucleic acid to certain parts of the cell. For example, agents can be used to disrupt endosomes and a nuclear localizing signal (NLS) can be used to target the nucleus.

A variety of ligands have been used to target drugs and genes to cells and to specific cellular receptors. The ligand may seek a target within the cell membrane, on the cell membrane or near a cell. Binding of ligands to receptors typically initiates endocytosis. Ligands could also be used for DNA delivery that bind to receptors that are not endocytosed. For example peptides containing RGD peptide sequence that bind integrin receptor could be used. In addition viral proteins could be used to bind the complex to cells. Lipids and steroids could be used to directly insert a complex into cellular membranes.

The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines.

Terminating Group of a Polymer

Is a group that is at the end of a polymer. The presence of these groups necessitate the end of the polymer. For example, every polyamino acid terminates with an amino group at one end and terminates with a carboxylic acid group at the other end.

Polyelectrolyte

A polyelectrolyte, or polyion, is a polymer possessing more than one charge, i.e. a polymer that contains groups that have either gained or lost one or more electrons. A polycation is a polyelectrolyte possessing net positive charge, for example PLL hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polyelectrolyte containing a net negative charge. The polyanion can contain monomer units that are charge negative, charge neutral, or charge positive, however, the net charge on the polymer must be negative. A polyanion can also mean a non-polymeric molecule that contains two or more negative charges. The term polyelectrolyte includes polycation, polyanion, zwitterionic polymers, and neutral polymers. The term zwitterionic refers to the product (salt) of the reaction between an acidic group and a basic group that are part of the same molecule.

Copolyelectrolyte

A copolyelectrolyte is a polyelectrolyte that contains both negative and positive charges.

Chelator

A chelator is a polydentate ligand, a molecule that can occupy more than one site in the coordination sphere of an ion, particularly a metal ion, primary amine, or single proton. Examples of chelators include crown ethers, cryptates, and non-cyclic polydentate molecules. A crown ether is a cyclic polyether containing (—X—(CR1–2)n)m units, where n=1–3 and m=3–8. The X and CR1–2 moieties can be substituted, or at a different oxidation states. X can be oxygen, nitrogen, or sulfur, carbon, phosphorous or any combination thereof. R can be H, C, O, S, N, P. A subset of crown ethers described as a cryptate contain a second (—X—(CR1–2)n)z strand where z=3–8. The beginning X atom of the strand is an X atom in the (—X—(CR1–2)n)m unit, and the terminal CH2 of the new strand is bonded to a second X atom in the (—X—(CR1–2)n)m unit. Non-cyclic polydentate molecules containing (—X—(CR1–2)n)m unit(s), where n=1–4 and m=1–8. The X and CR1–2 moieties can be substituted, or at a different oxidation states. X can be oxygen, nitrogen, or sulfur, carbon, phosphorous or any combination thereof.

Polychelator

A polychelator is a polymer associated with a plurality of chelators by an ionic or covalent bond and can include a spacer. The polymer can be cationic, anionic, zwitterionic, neutral, or contain any combination of cationic, anionic, zwitterionic, or neutral groups with a net charge being cationic, anionic or neutral, and may contain steric stabilizers, peptides, proteins, signals, or amphipathic compound for the formation of micellar, reverse micellar, or unilamellar structures. Preferably the amphipathic compound can have a hydrophilic segment that is cationic, anionic, or zwitterionic, and can contain polymerizable groups, and a hydrophobic segment that can contain a polymerizable group.

Steric Stabilizer

A steric stabilizer is a long chain hydrophilic group that prevents aggregation of final polymer by sterically hindering particle to particle electrostatic interactions. Examples include: alkyl groups, PEG chains, polysaccharides, alkyl amines. Electrostatic interactions are the non-covalent association of two or more substances due to attractive forces between positive and negative charges.

Biological, Chemical, or Biochemical Reactions

Biological, chemical, or biochemical reactions involve the formation or cleavage of ionic and/or covalent bonds.

Reactive

A compound is reactive if it is capable of forming either an ionic or a covalent bond with another compound. The portions of reactive compounds that are capable of forming covalent bonds are referred to as reactive functional groups.

Lipids

Lipids are compounds that are insoluble in water but soluble in organic solvent which have the general structure composed of two distinct hydrophobic sections, that is two separate sections of uninterrupted carbon-carbon bonds. The two hydrophobic sections are connected through a linkage that contains at least one heteroatom, that is an atom that is not carbon (e.g. nitrogen, oxygen, silicon, and sulfur). Examples include esters and amides of fatty acids and include the glycerides (1,2-dioleoylglycerol (DOG)), glycolipids, phospholipids (dioleoylphosphatidylethanolamine (DOPE)).

Hydrocarbon

Hydrocarbon means containing carbon and hydrogen atoms; and halohydrocarbon means containing carbon, halogen (F, Cl, Br, I), and hydrogen atoms.

Alkyl, Alkene, Alkyne, Aryl

Alkyl means any $sp^3$-hybridized carbon-containing group; alkenyl means containing two or more $sp^2$ hybridized carbon atoms; aklkynyl means containing two or more sp hybridized carbon atoms; aralkyl means containing one or more aromatic ring(s) in addition containing $sp^3$ hybridized carbon atoms; aralkenyl means containing one or more aromatic ring(s) in addition to containing two or more $sp^2$ hybridized carbon atoms; aralkynyl means containing one or more aromatic ring(s) in addition to containing two or more sp hybridized carbon atoms; steroid includes natural and unnatural steroids and steroid derivatives.

Steroid

A steroid derivative means a sterol, a sterol in which the hydroxyl moiety has been modified (for example, acylated), or a steroid hormone, or an analog thereof. The modification can include spacer groups, linkers, or reactive groups.

Carbohydrate

Carbohydrates include natural and unnatural sugars (for example glucose), and sugar derivatives (a sugar derivative means a system in which one or more of the hydroxyl groups on the sugar moiety has been modified (for example, but not limited to, acylated), or a system in which one or more of the hydroxyl groups is not present).

Polyoxyethylene

Polyoxyethylene means a polymer having ethylene oxide units (—$(CH_2CH_2O)_n$—, where n=2–3000).

Electron Withdrawing and Donating Groups

Electron withdrawing group is any chemical group or atom composed of electronegative atom(s), that is atoms that tend to attract electrons. Electron donating group is any chemical group or atom composed of electropositive atom(s), that is atoms that tend to attract electrons.

Resonance Stabilization

Resonance stabilization is the ability to distribute charge on multiple atoms through pi bonds. The inductive effective, in a molecule, is a shift of electron density due to the polarization of a bond by a nearby electronegative or electropositive atom.

Sterics

Steric hindrance, or sterics, is the prevention or retardation of a chemical reaction because of neighboring groups on the same molecule.

Activated Carboxylate

An activated carboxylate is a carboxylic acid derivative that reacts with nucleophiles to form a new covalent bond. Nucleophiles include nitrogen, oxygen and sulfur-containing compounds to produce ureas, amides, carbonates, carbamates, esters, and thioesters. The carboxylic acid may be activated by various agents including carbodiimides, carbonates, phosphoniums, and uroniums to produce activated carboxylates acyl ureas, acylphosphonates, acid anhydrides, and carbonates. Activation of carboxylic acid may be used in conjunction with hydroxy and amine-containing compounds to produce activated carboxylates N-hydroxysuccinimide esters, hydroxybenzotriazole esters, N-hydroxy-5-norbornene-endo-2,3-dicarboximide esters, p-nitrophenyl esters, pentafluorophenyl esters, 4-dimethylaminopyridinium amides, and acyl imidazoles.

Nucleophile

A nucleophile is a species possessing one or more electron-rich sites, such as an unshared pair of electrons, the negative end of a polar bond, or pi electrons.

Cleavage and Bond Breakage

Cleavage, or bond breakage is the loss of a covalent bond between two atoms. Cleavable means that a bond is capable of being cleaved.

Substituted Group or Substitution

A substituted group or a substitution refers to chemical group that is placed onto a parent system instead of a hydrogen atom. For the compound methylbenzene (toluene), the methyl group is a substituted group, or substitution on the parent system benzene. The methyl groups on 2,3-dimethylmaleic anhydride are substituted groups, or substitutions on the parent compound (or system) maleic anhydride.

Salt

A salt is any compound containing ionic bonds, that is bonds in which one or more electrons are transferred completely from one atom to another. Salts are ionic compounds that dissociate into cations and anions when dissolved in solution and thus increase the ionic strength of a solution.

Pharmaceutically Acceptable Salt

Pharmaceutically acceptable salt means both acid and base addition salts.

Pharmaceutically Acceptable Acid Addition Salt

A pharmaceutically acceptable acid addition salt is those salts which retain the biological effectiveness and properties of the free bases, and are not biologically or otherwise undesirable, and which are formed with inorganic acids such as hydrochloric acid, hydrobromic acis, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethansulfonic acid, p=toluenesulfonic acid, salicylic acid, trifluoroacetic acid, and the like.

Pharmaceutically Acceptable Base Addition Salt

A pharmaceutically acceptable base addition salt is those salts which retain the biological effectiveness and properties of the free acids, and are not biologically or otherwise undesirable. The salts are prepared from the addition of an inorganic base or an organic base to the free acid. Salts derived from inorganic bases include, but are not limited to, sodium, potassium, calcium, lithium, ammonium, magnesium, zinc, and aluminum salts and the like. Salts derived from organic bases include, but are not limited to salts of primary secondary, and tertiary amines, such as methylamine, triethylamine, and the like.

EXAMPLES

Synthesis of Polyampholyte MC#510

To a solution of poly(methyl vinyl ether-alt-maleic anhydride) (purchased from Aldrich Chemical) 50 mg in 10 mL of anhydrous tetrahydrofuran was added 100 mg of histamine. The solution was stirred for 1 hour followed by the addition of 10 mL water. The solution was stirred for another hour and then placed into a 12,000 MW cutoff dialysis tubing and dialyzed against 7×4L water over a one week period. The solution was then removed from the dialysis tubing and then concentrated to 1 mL volume by lyophilization.

Synthesis of Polyampholyte MC#486

To a solution of histidine (150 mg) and potassium carbonate (150 mg) in 10 mL water was added 50 mg of poly(methyl vinyl ether-alt-maleic anhydride) (purchased from Aldrich Chemical). The solution was stirred for 1 hour and then placed into a 12,000 MW cutoff dialysis tubing and dialyzed against 7×4L water over a one week period. The solution was then removed from the dialysis tubing and then concentrated to 1 mL volume by lyophilization.

Determination of the Charge Density of MC#486 and MC#510 as a Function of pH

To determine the effect of pH on MC#486 and MC#510, we measured the amount of polymer needed to compact fluorescein-labeled polylysine at pH 7.5 and pH 6.0. The fluorescein groups enabled us to measure the condensation of the polylysine: as the polylysine compacts the fluorescein groups are brought closer together thereby decreasing their fluorescence. Fluorescein-labeled PLL (40 μg/mL) in either 20 mM N-(2-Hydroxyethyl)piperazine-N'-(2-ethanesulfonic acid) (HEPES) buffer pH 7.5 or 20 mM MES buffer pH 6.0 was condensed by addition of increasing amounts of polyampholytes MC#486 and MC#510. After each addition of polyampholyte the fluorescence intensity of the fluorescein was measured at 530 nm (excitation at 495 nm). The histamine-containing polymer, MC#510, requires significantly more material to condense the polylysine at pH 6.0 than at pH 7.5. Approximately five-fold more polymer is required to condense polylysine at pH 6 than is required at pH 7.5. The histidine-containing polymer, MC#486, also need more material at pH 6.0, approximately two-fold more than the amount needed at pH 7.5. These data indicate that these polyampholytes are pH-titratable in the range 6–8.

Transfection with Polyampholytes MC#486 and MC#510

To a complex of plasmid DNA pCIluc (10 μg/mL, prepared according to Danko, I., Williams, P., Herweijer, H. Zhang, G., Latendresse, J. S., Bock, I., Wolff, J. A. *Hum. Mol. Genetics* 1997, 6, 1435.) and histone H1 (40 μg/mL) in 0.25 mL of 5 mM HEPES buffer pH 7.5 was added 15, 30 or 60 μg/mL polyampholytes MC#486 or MC#510. These complexes were then added (100 μL) to a well (12-well plates containing 1 mL media) containing mouse hepatoma hepa-1clc7 cells at 50% confluency in opti-MEM media. The cells were incubated for 4 hours in a humidified, 5% $CO_2$ incubator at 37° C. Then, the media was replaced with Dubelco's modified Eagle Media containing 10% fetal bovine serum, and the cells were incubated for 48 h. The cells were then harvested and the lysate was then assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. Each complex was tested in duplicate and the mean transfection efficiency was measured in relative light units (RLU).

| Concentration of polyampholyte | MC#486 | MC#510 |
| --- | --- | --- |
| 0 μg/mL | 1100 | 1100 |
| 15 μg/mL | 1313 | 2147 |
| 30 μg/mL | 14608 | 376459 |
| 60 μg/mL | 33630 | 200895 |

Synthesis of Polyallylamine-Graft Imidazoleacetic Acid Polycation (DW#163)

Polyallylamine (15,000 MW) is dissolved to 50 mg/mL in 100 mM MES (p)H 6.5) buffer in a 15-ml polypropylene tube. To this solution is added 1.1 molar equivalent (relative to amine content of polyallylamine) of 4-imidazoleacetic acid. N-(3-Dimethylaminopropyl)-N'-ethylcarbodiimide (EDC) (1.1 equivalent) and N-hydroxysuccinimide (1.1 equivalent) are dissolved in 2 ml of MES buffer and are added immediately to the polyallylamine solution. The reaction tube was sealed and allowed to react at room temperature for 24 hours. The reaction mixture is then removed from tube and placed into dialysis tubing (3,500 MW cutoff), and dialyzed against 7×4 L water over a one week period. The polymer is then removed from the tubing and concentrated by lyophilization to 10 mg/mL. This polymer is given the number DW#163.

Synthesis of Polyampholyte MC#750

To a solution of poly(methyl vinyl ether-alt-maleic anhydride) (purchased from Aldrich Chemical) 50 mg in 10 mL of anhydrous tetrahydrofuran was added 100 mg of 1-(3-aminopropyl)imidazole. The solution was stirred for 1 hour followed by the addition of 10 mL water. The solution was stirred for another hour and then placed into a 12,000 MW cutoff dialysis tubing and dialyzed against 7×4L water over a one week period. The solution was then removed from the dialysis tubing and then concentrated to 1 mL volume by lyophilization. This polymer was given number MC#750

Transfection with Polyampholytes MC#510 and MC#750

To a complex of plasmid DNA pCIluc (10 μg/mL, prepared according to Danko, I., Williams, P., Herweijer, H. Zhang, G., Latendresse, J. S., Bock, I., Wolff, J. A. *Hum. Mol. Genetics* 1997, 6, 1435.) and polycation DW#163 (40 μg/mL) in 0.25 mL of 5 mM HEPES buffer pH 7.5 was added 40 or 80 μg/mL polyampholytes MC#510 or MC#750. These complexes were then added (100 μL) to a well (12-well plates containing 1 mL media) containing mouse hepatoma hepa-1clc7 cells at 50% confluency in opti-MEM media. The cells were incubated for 4 hours in a humidified, 5% $CO_2$ incubator at 37° C. Then, the media was replaced with Dubelco's modified Eagle Media containing 10% fetal bovine serum, and the cells were incubated for 48 h. The cells were then harvested and the lysate was then assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. Each complex was tested in duplicate and the mean transfection efficiency was measured in relative light units (RLU).

| Concentration of polyampholyte | MC#510 | MC#750 |
| --- | --- | --- |
| 0 μg/mL | 116,377 | 116,377 |
| 40 μg/mL | 2,549,900 | 6,757,028 |
| 80 μg/mL | 1,664,432 | 30,119 |

Synthesis of Polyampholytes from the Polyampholyte MC#510 and the Polyeation PLL.

To test the transfection ability of an alternating polyampholyte (MC#510) and to construct and test a block polyampholyte made from an alternating polyampholyte, samples were made according the following table.

| Sample name | Composition |
| --- | --- |
| 1:4 (PLL:MC#510) pH 8 | 100 μg PLL, 400 μg MC#510 and 1.8 M NaCl (V = 11 μL) |
| 1:4 (PLL:MC#510) pH 8-EDC | 100 μg PLL, 400 μg MC#510, 1.9 M NaCl, and 5 μg EDC (V = 16 μL) |
| 1:4 (PLL:MC#510) pH 6 | 100 μg PLL, 400 μg MC#510, 1 M NaCl, and 225 mM MES buffer pH 5 (V = 20 μL) |
| 1:4 (PLL:MC#510) pH 6-EDC | 100 μg PLL, 400 μg MC#510, 1.5 M NaCl, 5 μg EDC, and 155 mM MES buffer pH 5 (V = 29 μL) |
| 1:2 (PLL:MC#510) pH 8 | 100 μg PLL, 200 μg MC#510, and 2.5 M NaCl (V = 8 μL) |
| 1:2 (PLL:MC#510) pH 8-EDC | 100 μg PLL, 200 μg MC#510, 2.7 M NaCl, and 5 μg EDC (V = 17 μL) |
| 1:2 (PLL:MC#510) pH 6 | 100 μg PLL, 200 μg MC#510, 2.5 M NaCl, and 214 mM MES (V = 14 μL) |
| 1:2 (PLL:MC#510) pH 6-EDC | 100 μg PLL, 200 μg MC#510, 2.0 M NaCl, 130 mM MES, and 5 μg EDC (V = 23 μL) |
| 1:1 (PLL:MC#510) pH 8 | 100 μg PLL, 100 μg MC#510, and 2.2 M NaCl (V = 4.5 μL) |
| 1:1 (PLL:MC#510) pH 8-EDC | 100 μg PLL, 100 μg MC#510, 2.7 M NaCl, and 5 μg EDC (V = 13 μL) |
| 1:1 (PLL:MC#510) pH 6 | 100 μg PLL, 100 μg MC#510, 1.0 M NaCl, and 285 mM MES (V = 10.5 μL) |

| Sample name | Composition |
|---|---|
| 1:1 (PLL:MC#510) pH 6-EDC | 100 µg PLL, 100 µg MC#510, 1.8 M NaCl, 158 mM MES, and 5 µg EDC (V = 19 µL) |

The stock solution of MC#510 was at pH 8, which caused samples to be at pH 8 unless buffered otherwise. Samples at pH 6 were buffered by the addition of a stock solution of 2-(N-Morpholino)ethanesulfonic acid (MES) buffer 500 mM at pH 5, which brought the pH of the samples down to approximately pH 6. A block-type polyampholyte was formed by the addition of N-(3-Dimethylaminopropyl)-N'-ethylcarbodiimide (EDC), which forms an amide bond between the carboxylates of MC#510 and the amines of PLL.

Transfection of Polyampholytes from the Polyampholyte MC#510 and the Polycation PLL.

To a solution of plasmid DNA pCIluc (10 µg/mL, prepared according to Danko, I., Williams, P., Herweijer, H. Zhang, G., Latendresse, J. S., Bock, I., Wolff, J. A. *Hum. Mol. Genetics* 1997, 6, 1435.) was added polyampholytes as prepared above. The amount of PLL added was constant, 30 µg/mL. These complexes were then added (100 µL) to a well (12-well plates containing 1 mL media) containing mouse hepatoma HEPA-1clc7 cells at 50% confluency in opti-MEM media. The cells were incubated for 4 hours in a humidified, 5% CO2 incubator at 37° C. The media was then replaced with Dubelco's modified Eagle Media containing 10% fetal bovine serum. The cells were then incubated for 48 h. The cells were then harvested and the lysate was then assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. Each complex was tested in duplicate and the mean transfection efficiency was measured in relative light units (RLU).

| Sample name | RLU serum free | RLU in 10% serum |
|---|---|---|
| 1:4 (PLL:MC#510) pH 8-EDC | 253,465 | 1,744,427 |
| 1:4 (PLL:MC#510) pH 8 | 210,195 | 691,744 |
| 1:4 (PLL:MC#510) pH 6-EDC | 49,510 | 2,209,812 |
| 1:4 (PLL:MC#510) pH 6 | 183,217 | 1,714,226 |
| 1:2 (PLL:MC#510) pH 8-EDC | 88,443 | 7,820,140 |
| 1:2 (PLL:MC#510) pH 8 | 32,266 | 4,770,977 |
| 1:2 (PLL:MC#510) pH 6-EDC | 504,809 | 13,067 |
| 1:2 (PLL:MC#510) pH 6 | 298,997 | 1,442,482 |
| 1:1 (PLL:MC#510) pH 8-EDC | 413,114 | 1,905 |
| 1:1 (PLL:MC#510) pH 8 | 118,656 | 1,846 |
| 1:1 (PLL:MC#510) pH 6-EDC | 356,970 | 2,862 |
| 1:1 (PLL:MC#510) pH 6 | 41,785 | 1,813 |

Intravascular Delivery of a Polyampholyte

To a solution of plasmid DNA pCIluc (10 µg, prepared according to Danko, I., Williams, P., Herweijer, H. Zhang, G., Latendresse, J. S., Bock, I., Wolff, J. A. *Hum. Mol. Genetics* 1997, 6, 1435.) was added polyampholyte 1:4 (PLL:MC#510) pH 6-EDC as prepared above or the polycation PLL. The amount of PLL added was 30 µg and the amount of MC#510 was 120 µg. These complexes were then added to 2 mL Ringer's solution and injected into the tail vein of ICR mice (20 gm weight on average). After 24 hours, the animals were sacrificed and their livers were assayed for luciferase activity.

| Complex | Relative light units |
|---|---|
| PLL alone | 847 |
| 1:4 (PLL:MC#510) pH 6-EDC | 56,241 |

In Vivo Transfection with Polycation DW#163 and Polyampholyte MC#510

A complexes of plasmid DNA pCIluc, polycation DW#163, and polyampholyte MC#510 were made at ratios as described below. The complexes were then injected into the bile duct of ICR mice (20 gm average per animal). The volume of injection was 200 µL, which was injected in 30 seconds. After 24 hours, the animals were sacrificed and the luciferase activity in the liver of each animal was measured.

| µg DNA/µg 163/µg 510 | RLU in liver (average of two animals) |
|---|---|
| 20/50/0 | 356,808 |
| 20/50/15 | 1,148,276 |
| 20/50/30 | 1,699,328 |

Synthesis of Acetal-Containing Polyampholyte DW#179A and B

To a solution of poly(methyl vinyl ether-alt-maleic anhydride) (purchased from Aldrich Chemical) 20 mg in 5 mL of anhydrous tetrahydrofuran was added 1.4 or 3.5 uL of aminoacetaldhyde dimethyl acetal (0.01 or 0.025 mol eq.) and this solution was stirred for 3 hours followed by the addition of 80 mg of histamine. The solution was then stirred for 24 hours followed by the addition of 10 mL water. The solution was stirred for another hour and then placed into a 12,000 MW cutoff dialysis tubing and dialyzed against 7×4L water over a one week period. The solution was then removed from the dialysis tubing and then concentrated to 1 mL volume by lyophilization. The polyampholyte containing 0.01 eq acetal was given the number DW#179A and the polyampholyte containing 0.025 eq acetal was given the number DW#179B.

Acetal Removal From DW#179A and B

The acetal groups of DW#179 were removed to produce aldehyde groups by placing 1 mg of DW179 into 1 mL centrifuge tube, and adjusting the pH to 3.0 with 1M HCl and left at room temperature 12 hrs. After incubation at acidic pH, the DW#179 may be added to polyamine-condensed DNA to form a schiff between the amine and the aldhyde thus forming a polyampholyte.

Transfection with Polycation DW#163 and Aldehyde-Containing Polyampholyte DW#179

To a complex of plasmid DNA pCIluc (10 µg/mL, prepared according to Danko, I., Williams, P., Herweijer, H. Zhang, G., Latendresse, J. S., Bock, I., Wolff, J. A. *Hum. Mol. Genetics* 1997, 6, 1435.) and polycation DW#163 (40 µg/mL) in 0.25 mL of 10 mM CHES pH 9.0 and 125 mM NaCl was added 40 or 80 µg/mL polyampholytes DW#179A or DW#179B. Half of the polyampholytes had the acetal groups removed to produce aldehyde groups, and the other half retained the acetal groups. These complexes were then added (100 µL) to a well (12-well plates containing 1 mL media) containing mouse hepatoma hepa-1clc7 cells at 50% confluency in opti-MEM media. The cells were incubated for 4 hours in a humidified, 5% $CO_2$ incubator at 37° C. Then, the media was replaced with Dubelco's modified Eagle Media containing 10% fetal bovine serum, and the cells were incubated for 48 h. The cells were then harvested and the lysate was then assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. Each complex was tested in duplicate and the mean transfection efficiency was measured in relative light units (RLU).

| Samples | aldehyde | Ratio | RLU |
|---|---|---|---|
| DNA/DW#163/DW#179A | − | 10/40/40 | 2164589 |
| DNA/DW#163/DW#179A | − | 10/40/80 | 645 |
| DNA/DW#163/DW#179A | + | 10/40/40 | 6327012 |
| DNA/DW#163/DW#179A | + | 10/40/80 | 282497 |
| DNA/DW#163/DW#179B | − | 10/40/40 | 402416 |
| DNA/DW#163/DW#179B | − | 10/40/80 | 550 |
| DNA/DW#163/DW#179B | + | 10/40/40 | 4844079 |
| DNA/DW#163/DW#179B | + | 10/40/80 | 2939 |

+ = aldehyde;
− acetal

Synthesis of Poly(Acrylic acid-co-maleic acid) Graft Histamine Polymer (MC#758)

A solution of Poly(Acrylic acid-co-maleic acid)(0.050 g, 0.026 mmol), histamine (0.029 g, 0.026 mmol) were dissolved in 5 mL of 100 mM 2-[N-morpholino] ethanesulfonic acid(MES) at pH 6.5. This solution was then added to 1,[3-(dimethylamino)propyl]-3-ethylcarboimide(EDC)(0.057 g, 0.029 mmol), followed by the addition of N-hydroxysuccinimide(NHS) (0.033 g, 0.029 mmol) in 0.5 mL of pH 6.5 100 mM MES. This solution was sealed tightly and stirred for 24 hours at room temperature. This solution was then transferred to 12,000 to 14,000 molecular weight tubing and dialyzed against distilled water for 4 days, and freeze dried. This polyampholyte was given the number MC#758.

Synthesis of Poly(Acrylic acid-co-maleic acid) Graft 1-(3-amino-propyl)imidazole polymer (MC#757)

Poly(Acrylic acid-co-maleic acid)(0.050 g, 0.026 mmol), and 1-(3-amino-propyl) imidazole (0.0155 g, 0.013 mmol) were dissolved in 5 mL of 100 MES at pH 6.5. This solution was then added to 1,[3-(dimethylamino)propyl]-3-ethylcarboimide(EDC)(0.0312 g, 0.016 mmol), followed by the addition of N-hydroxysuccinimide(NHS)(0.012 g, 0.016 mmol) in 0.5 mL of pH 6.5 100 mM MES. This solution was sealed tightly and stirred for 24 hours at room temperature. This solution was then transferred to 12,000 to 14,000 molecular weight tubing and dialyzed against distilled water for 4 days, and freeze dried. This polyampholyte was given the number MC#757.

In vivo Transfection Using Polyampholytes MC#757 and MC#758

A complexes of plasmid DNA pCIluc, polycation linear polyethyleneimine (1-PEI), and polyampholytes MC#757 and MC#758 were made at ratios as described below. The complexes were then injected into the tail vein of ICR mice (20 gm average per animal). The injection solution was 250 µL and contained 10 mM HEPES pH 7.5 and 290 mM glucose. The concentration of DNA was 200 µg/mL. Thirty minutes after DNA injection a second injection was made of 1.5 mg poly(acrylic acid) in 100 µL solution of 10 mM HEPES pH 7.5 and 290 mM glucose. After 24 hours, the animals were sacrificed and the luciferase activity in the lung of each animal was measured.

| Samples | Weight Ratios (µg) | RLU Lung |
|---|---|---|
| DNA/1-PEI/ | 50/400/ | 4046700 |
| DNA/1-PEI/poly(acrylic acid) | 50/400/50 | 16601610 |
| DNA/1-PEI/MC#757 | 50/400/25 | 11774597 |
| DNA/1-PEI/MC#758 | 50/400/50 | 7462460 |
| DNA/1-PEI/MC#757 | 50/400/50 | 19586710 |
| DNA/1-PEI/MC#757 | 50/400/75 | 28837510 |
| DNA/1-PEI/MC#757 | 50/400/100 | 44823516 |
| DNA/1-PEI/MC#757 | 50/400/150 | 66175376 |

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Various modifications of the described modes for carrying out the invention which are obvious to those skilled in cell biology, chemistry, molecular biology, biochemistry or related fields are intended to be within the scope of the following claims.

We claim:

1. A process for enhancing delivery of a polyion to a cell, comprising:
   a) forming a complex of polyion and polyampholyte that is pH-titratable at physiological pH; and,
   b) delivering the complex into a cell.

2. The process of claim 1 wherein the polyion is DNA.

3. The process of claim 1 wherein the polyampholyte contains imidazole groups.

4. The process of claim 1 wherein the polyampholyte contains imidazole derivatives.

5. The process of claim 1 wherein the polyampholyte is anionic at pH 8.

6. The process of claim 1 wherein the polyampholyte is membrane active.

7. The process of claim 1 wherein the polyampholyte is delivered to a cell in vivo.

8. A complex for delivering a polyion to a cell, comprising: a polyion; and, a polyampholyte that is pH-titratable at physiological pH.

9. The complex of claim 8 wherein the polyion is DNA.

10. The complex of claim 8 wherein the polyampholyte contains imidazole groups.

11. The complex of claim 8 wherein the polyampholyte contains imidazole derivatives.

12. The complex of claim 8 wherein the polyampholyte is anionic at pH 8.

13. The complex of claim 8 wherein the polyampholyte is membrane active.

14. A process for extravasation of a complex, comprising:
   a) forming a complex of polyion and polyampholyte wherein the polyampholyte is pH-titratable at physiological pH;
   b) inserting the complex into a vessel; and,
   c) delivering the complex to an extravascular space.

15. The process of claim 14 wherein the polyion is DNA.

16. The process of claim 14 wherein the polyampholyte contains imidazole groups.

17. The process of claim 14 wherein the polyampholyte contains imidazole derivatives.

18. The process of claim 14 wherein the polyampholyte is membrane active.

19. The process of claim 15 wherein the DNA is expressed in an extravascular cell.

20. The process of claim 14 wherein the polyampholyte is anionic at pH 8.

* * * * *

SEQUENCE LISTING

<160> NUMBER OF SEQ ID NOS: 8

<210> SEQ ID NO 1
<211> LENGTH: 13
<212> TYPE: PRT
<213> ORGANISM: Simian virus 40

<400> SEQUENCE: 1

Cys Gly Tyr Gly Pro Lys Lys Lys Arg Lys Val Gly Gly
1               5                   10

<210> SEQ ID NO 2
<211> LENGTH: 39

```
<212> TYPE: PRT
<213> ORGANISM: Simian virus 40

<400> SEQUENCE: 2

Cys Lys Lys Lys Ser Ser Ser Asp Asp Glu Ala Thr Ala Asp Ser Gln
1               5                   10                  15

His Ser Thr Pro Pro Lys Lys Lys Arg Lys Val Glu Asp Pro Lys Asp
            20                  25                  30

Phe Pro Ser Glu Leu Leu Ser
        35

<210> SEQ ID NO 3
<211> LENGTH: 37
<212> TYPE: PRT
<213> ORGANISM: Simian virus 40

<400> SEQUENCE: 3

Cys Lys Lys Lys Trp Asp Asp Glu Ala Thr Ala Asp Ser Gln His Ser
1               5                   10                  15

Thr Pro Pro Lys Lys Lys Arg Lys Val Glu Asp Pro Lys Asp Phe Pro
            20                  25                  30

Ser Glu Leu Leu Ser
        35

<210> SEQ ID NO 4
<211> LENGTH: 31
<212> TYPE: PRT
<213> ORGANISM: Homo sapiens

<400> SEQUENCE: 4

Cys Tyr Asn Asp Phe Gly Asn Tyr Asn Asn Gln Ser Ser Asn Phe Gly
1               5                   10                  15

Pro Met Lys Gln Gly Asn Phe Gly Gly Arg Ser Ser Gly Pro Tyr
            20                  25                  30

<210> SEQ ID NO 5
<211> LENGTH: 10
<212> TYPE: PRT
<213> ORGANISM: Human adenovirus type 5

<400> SEQUENCE: 5

Cys Lys Arg Gly Pro Lys Arg Pro Arg Pro
1               5                   10

<210> SEQ ID NO 6
<211> LENGTH: 22
<212> TYPE: PRT
<213> ORGANISM: Xenopus laevis

<400> SEQUENCE: 6

Cys Lys Lys Ala Val Lys Arg Pro Ala Ala Thr Lys Lys Ala Gly Gln
1               5                   10                  15

Ala Lys Lys Lys Lys Leu
            20

<210> SEQ ID NO 7
<211> LENGTH: 14
<212> TYPE: PRT
<213> ORGANISM: Homo sapiens
```

```
<400> SEQUENCE: 7

Cys Lys Lys Lys Gly Pro Ala Ala Lys Arg Val Lys Leu Asp
1               5                   10

<210> SEQ ID NO 8
<211> LENGTH: 4
<212> TYPE: PRT
<213> ORGANISM: Homo sapiens

<400> SEQUENCE: 8

Lys Asp Glu Leu
1
```